United States Patent
Mille et al.

(10) Patent No.: US 6,645,912 B1
(45) Date of Patent: Nov. 11, 2003

(54) HERBICIDAL COMPOSITIONS

(76) Inventors: Fabien Hervé Joseph Mille, 1 Porte au Rupt, F-55200 Commercy (FR); Philip James Oxford, 141 Carlyle Road, South Ealing, London W5 4BP (GB)

( * ) Notice: Subject to any disclaimer, the term of this patent is extended or adjusted under 35 U.S.C. 154(b) by 487 days.

(21) Appl. No.: 10/018,556

(22) PCT Filed: Jul. 28, 2000

(86) PCT No.: PCT/GB00/02865
§ 371 (c)(1),
(2), (4) Date: Apr. 17, 2002

(87) PCT Pub. No.: WO01/08482
PCT Pub. Date: Feb. 8, 2001

(30) Foreign Application Priority Data

Jul. 31, 1999 (GB) .............................................. 9917976

(51) Int. Cl.⁷ .......................... A01N 25/30; A01N 57/02

(52) U.S. Cl. ........................................ 504/206; 504/362
(58) Field of Search .................................. 504/206, 362

(56) References Cited

U.S. PATENT DOCUMENTS 5,998,332 A * 12/1999 Sato et al. ................... 504/127
6,093,679 A * 7/2000 Azuma et al. ............... 504/116

FOREIGN PATENT DOCUMENTS

EP 0 560 570 * 9/1993

* cited by examiner

*Primary Examiner*—S. Mark Clardy
(74) *Attorney, Agent, or Firm*—Russ R. Stolle; Ron D. Brown; Christopher J. Whewell

(57) ABSTRACT

Amido alkyl amine oxides, optionally blended with ether carboxylates, amphoteric surfactants, chelants, solvents, hydrotropes and/or wetting agents are used to prepare glyphosate solution concentrates.

20 Claims, No Drawings

HERBICIDAL COMPOSITIONS

This application has been filed under 35 USC 371 as the national stage of international application PCT/GB00/02865, filed Jul. 28, 2000.

The present invention relates to concentrated herbicidal compositions comprising water soluble glyphosate salts and a surfactant.

A number of formulations have been proposed whereby the herbicide N-(phosphonomethyl)glycine, alias glyphosate, may be supplied as a concentrated aqueous solution with a surfactant synergist which aids wetting and penetration, when the composition is diluted with water and applied to herbage.

The surfactants which have so far proved most cost effective for these purposes have been ethoxylated amines. The latter however have a poor environmental profile being biotoxic and poorly biodegradable. There is a demand for a more environmentally acceptable alternative to amine ethoxylates.

Factors governing the choice of surfactant include wetting power, herbicidal or synergistic action, environmental profile and ability to form stable solutions with glyphosate at as high a concentration as possible, as well as cost. A particularly important factor is low foaming. Most surfactants cause undesirable foam levels. These not only make handling more difficult but also impair biocidal effectiveness.

The use of trihydrocarbyl amine oxides has been proposed in WO 97/36491. However these have been found to give undesirably viscous compositions at economically desirable concentrations.

We have discovered that ether carboxylates meet most of the above criteria and in particular give enhanced biocidal action but are insufficiently soluble in concentrated glyphosate solutions. We have found (see WO/00/38523) that betaines can solubilise ether carboxylates, but that high salt levels normally associated with betaines tend to precipitate glyphosate. Desalted betaines are available but are expensive. We have now discovered that certain alkyl amido amine oxides also meet most of the above criteria and in addition are soluble and can act as cosurfactants, solubilising ether carboxylates. The trihydrocarbyl amine oxides are not readily compatible with ether carboxylates.

The invention provides a herbicidal solution concentrate comprising from 30% by weight, to saturation of a water soluble glyphosate salt and from 8 to 20% by weight of surfactant comprising: 10 to 100% by weight based on the total weight of surfactant of an alkyl and/or alkenyl amido amine oxide of the formula:

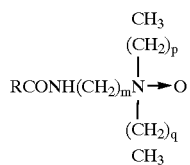

where R is a $C_{6-20}$ alkyl or alkenyl group, m is 1 to 4, and p and q are independently 0 to 3; and from 0 to 90% by weight based on the total weight of surfactant of ether carboxylate.

The glyphosate is preferably present as its potassium, ammonium, $C_{2\ to\ 3}$ amine or mono or di ethanolamine salt, or as a mixture of two or more of said salts. Particularly preferred is the isopropylamine salt.

We prefer that (m + the number of carbon atoms in R) is from 7 to 19 and that p and q are each 0. We particularly prefer that m is 2 or most preferably 3. R is desirably 8 or 10. Amine oxides in which the majority of the amido alkyl groups are of the same length are particularly preferred. Especially preferred are N-octanoamidopropyl-N,N-dimethyl amine oxide, and N-decanoamidopropyl-N,N-dimethyl amine oxide. The amine oxide may optionally be derived from a coconut or palm fatty acid, especially one which has been "topped", i.e. has had the higher mol weight constituents such as $C_{14}+$, removed or reduced.

We prefer that the amine oxide should constitute at least 20 and preferably more than 30% by weight of the total surfactant especially 40 to 80%.

The presence of an ether carboxylate is preferred, since it provides enhanced biocidal activity. The ether carboxylate preferably constitutes at least 10%, more preferably greater than 20, especially more than 30% of the total weight of surfactant.

The ether carboxylate is an alkyl alkenyl or alkaryl poly alkoxy carboxylate such as $RO[(CH_2)_nO]_mCH_2CO^-_2$ where R is an alkyl, alkenyl or alkyl phenyl group having from 8 to 20 aliphatic carbon atoms, each n is 2 to 4, preferably 2 and m is 1 to 30, preferably 2 to 20, e.g. 3 to 10. The counter ion may comprise sodium but is preferably potassium or ammonium or an amine e.g. a $C_2$ to $_3$ amine or an alkanolamine. We particularly prefer narrow cut $C_8$ and $C_{10}$ alkyl polyethoxy carboxylates.

The surfactant may additionally comprise an amphoteric surfactant. The amphoteric surfactant may for example be a betaine, e.g. a betaine of the formula: $R_3N^{+CH}{}_2COO$, wherein each R is an alkyl, cycloalkyl, alkenyl or alkaryl group and preferably at least one, and most preferably not more than one R, has an average of from 6 to 14, e.g. 8 to 10 aliphatic carbon atoms and each other R has an average of from 1 to 4 carbon atoms. It may also comprise a so called "imidazoline" betaine traditionally ascribed the formula:

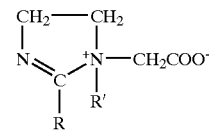

wherein R and R' are alkyl, alkenyl, cycloalkyl, alkaryl or alkanol groups having an average of from 1 to 20 aliphatic carbon atoms and R preferably has an average of from 6 to 20, e.g. 8 to 14 aliphatic carbon atoms and R' preferably has 1 to 4 carbon atoms. In practise "imidazoline" betaines are normally present substantially entirely as the non-cylic N-amido-alkyl betaine. Other amphoteric surfactants for use according to our invention include alkyl amino polyalkoxy sulphates, sulphobetaines and other quaternary amine or quaternised imidazoline sulphonic acids and their salts, and Zwitterionic surfactants, e.g. N-alkyl taurines, carboxylated amido amines such as $RCONH(CH_2)_nN^{+R'}{}_2CH_2CO^-_2$ where n is 2 to 4, and amino acids having, in each case, hydrocarbon groups capable of conferring surfactant properties (e.g. alkyl, cycloalkyl alkenyl or alkaryl groups having from 8 to 20 aliphatic carbon atoms). Typical examples include 2-tallow alkyl, 1-tallow amido alkyl, 1-carboxymethyl imidazoline, 2-coconut alkyl N-carboxymethyl2 (hydroxyalkyl)imidazoline, coconut amido propyl dimethyl betaine and $C_{12-14}$ alkyl dimethyl betaine. Generally speaking any water soluble amphoteric or Zwitterionic surfactant compound which comprises a hydrophobic portion including $C_{8-20}$ alkyl or alkenyl group and a hydrophilic portion containing an amine or quaternary ammonium group and a carboxylate, sulphate or sulphonic acid group may be used in our invention.

The amphoteric surfactant may constitute from 0 to 90% more usually less than 90%, preferably less than 70%, especially less than 50% by weight of the total surfactant.

It is strongly preferred when an amphoteric surfactant is selected to use a low sodium version, to avoid precipitation of sodium glyphosate. Typically the concentration of sodium ion in the composition should be less than 0.035% based on the total weight of the composition.

We prefer that the surfactant consist essentially of the amine oxide, ether carboxylate and, optionally, the amphoteric surfactant. We do not, however, exclude the presence of minor amounts, e.g. up to 15%, preferably less than 10% by weight of the total surfactant, of other surfactants such as non-ionic surfactants including alkylethoxylates and alkanolamides and anionic surfactants such as alkyl ether sulphates, alkyl sulphates, alkyl benzene sulphonates and soaps. In particular it is often advantageous to include up to 15% by weight of a wetting agent.

The formulation may conveniently contain chelating or sequestering agents to enhance the performance of the product in hard water. For example calcium and/or magnesium sequestrants, such as phosphates, polyphosphates, polycarboxylates, amino carboxylates, phosphonates and, in particular, amino phophonates, may be present in effective amounts. Specific examples include potassium pyrophosphate, sodium tripolyphosphate, ammonium hexametaphosphate, citric acid, polyacrylic acid nitrilotriacetic acid, ethylene diamine tetracetic acid, acetodiphosphonic acid, amino tris (methylenephosphonic) acid, ethylene diamine tetrakis (methylene phosphonic) acid and especially diethylene triamine pentakis (methylene phosphonic) acid.

The chelant may be present in the acid form or as a water soluble salt, however for reasons stated above we prefer that the amount of sodium be limited: We therefore prefer that the chelant if present as a salt be present as the potassium or more preferably ammonium salt or as an amine or alkalolarnine salt. The chelant is preferably present in concentrations of from 0.05 to 5% especially 0.1 to 1% e.g. 0.2 to 0.5%.

The solution concentrate does not normally require the presence of solvents, however they can be tolerated and may be adventitiously present as constituents of surfactant blends used to prepare the solution concentrates.

We generally prefer to supply surfactants for use in the preparation of the solution concentrates in the form of concentrated blends. The latter may require small amounts of solvent for stability. Typically the blends contain: from 10 to 70% more preferably 20 to 60% e.g. 30 to 50% ether carboxylate by weight of the blend; from 20 to 80% more preferably 30 to 70% e.g. 40 to 60% of the amidoalkyl amine oxide by weight of the blend; and from 3 to 50% more preferably 5 to 40% e.g. 10 to 30%, by weight of the blend, of solvent.

The solvent is typically a water miscible mono, di- or polyhydric alcohol or glycol ether such as ethanol, ispropanol, ethylene glycol, glycerol, ethylene glycol monomethyl ether, diethylene glycol monomethyl ether or preferably polyethylene glycol. We prefer a polyethylene glycol with a mean molecular weight of from 90 to 300, e.g. 130 to 250.

The surfactant blend may optionally contain minor amounts of hydrotrope such as a $C_1$ to $_5$ alkyl benzene sulphonate e.g. a potassium, ammonium or amine xylene sulphonate, if required to inhibit gelling. We prefer to use the minimum amount required to achieve the desired effect which will usually be between 0.1 and 5% of the weight of the blend.

The invention provides the use of blends of ether carboxylate and amidoalkyl amine oxide to prepare glyphosphate solution concentrates and to such blends for use in preparing the concentrates and to sprayable solutions prepared by diluting the solution concentrate with water.

We prefer that the pH of the solution concentrate be adjusted to from 3 to 7 preferably 4 to 6 e.g. 4.5 to 5.5 with a base that does not precipitate glyphosate, such as ammonia or an amine.

The invention will be illustrated by the following examples in which the glyphosate was used as the isopropylamine salt and weights of glyphosate are all quoted as gm acid equivalent per litre solution. Surfactants and glycol are all quoted as g. active matter per litre of solution.

"EMPICOL" is a Registered Trade Mark of Albright & Wilson UK Limited

CVE is $C_8$ alkyl 5 mole ethoxy carboxylate

CVH is $C_8$ alkyl 8 mole ethoxy carboxylate

"$C_8$ amido amine oxide" is N-octanoamidopropyl-N, Ndimethylamine oxide

"$C_{10}$ amido amine oxide" is N-decanoamidopropyl-N, Ndimethylamine oxide

Example 1

| | |
|---|---|
| Glyphosate | 360 |
| $C_8$ amidoamine oxide | 75 |
| "EMPICOL" CVE | 75 |
| PEG 200 | 40 |
| Water | to 1l |
| Ammonia solution | to pH 5 |

Example 2

| | |
|---|---|
| Glyphosate | 360 |
| $C_8$ amidoamine oxide | 50 |
| "EMPICOL" CVE | 100 |
| PEG 200 | 40 |
| Water | to 1l |
| Ammonia solution | to pH 5 |

Example 3

| | |
|---|---|
| Glyphosate | 360 |
| C8 amidoamine oxide | 43 |
| "EMPICOL" CVE | 107 |
| PEG 200 | 40 |
| Water | to 1l |
| Ammonia solution | to pH 5 |

Example 4

| | |
|---|---|
| Glyphosate | 360 |
| $C_8$ amidoamine oxide | 35.7 |
| "EMPICOL" CVE | 89.3 |
| Water | to 1l |
| Ammonia solution | to pH 5 |

Example 5

| | |
|---|---|
| Glyphosate | 360 |
| C$_8$ amidoamine oxide | 75 |
| "EMPICOL" CVH | 75 |
| PEG200 | 40 |
| Water | to 1l |
| Ammonia solution | to pH 5 |

Example 6

| | |
|---|---|
| Glyphosate | 360 |
| C$_{10}$ amidoamine oxide | 75 |
| "EMPICOL" CVE | 75 |
| PEG 200 | 40 |
| Water | to 1l |
| Ammonia solution | to pH 5 |

Example 7

| | |
|---|---|
| Glyphosate | 360 |
| C$_{10}$ amidoamine oxide | 50 |
| "EMPICOL" CVE | 100 |
| PEG 200 | 40 |
| Water | to 1l |
| Ammonia solution | to pH 5 |

Example 8

| | |
|---|---|
| Glyphosate | 360 |
| C$_{10}$ amidoamine oxide | 75 |
| "EMPICOL" CVH | 75 |
| PEG200 | 40 |
| Water | to 1l |
| Ammonia solution | to pH 5 |

Example 9

| | |
|---|---|
| Glyphosate | 360 |
| "EMPICOL" CVH | 100 |
| C$_{10}$ amidoamine oxide | 50 |
| "BRIQUEST" 301-50A | 5.5 |
| PEG200 | 40 |
| Water | to 1L |
| Ammonia solution | to pH 5 |

Example 10

| | |
|---|---|
| Glyphosate | 360 |
| "EMPICOL" CVH | 69.1 |
| C$_{10}$ amidoamine oxide | 50 |
| "EMPILAN" KI 6.5 | 5.5 |
| PEG200 | 40 |
| Water | to 1L |
| Ammonia solution | to pH 5 |

Each of the above formulations was a clear, stable solution which gave very low foam in comparison to the standard commercial product. In each case the formulation was prepared from a blend of the ether carboxylate (which is supplied as 85% aqueous solution) amine oxide (as 40% aqueous solution) and any solvent, chelant or wetting agent.

The blends were stable and dispersed easily in water together with the glyphosate.

The pH of the formulation was finally adjusted with ammonia.

What is claimed is:

1. A herbicidal solution concentrate comprising from 30% by weight, to saturation of a water soluble glyphosate salt and from 8 to 20% by weight of surfactant comprising: 10 to 100% by weight based on the total weight of surfactant of an alkyl and/or alkenyl amido amine oxide of the formula:

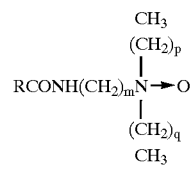

where R is a C$_{6-20}$ alkyl or alkenyl group, m is 1 to 4, and p and q are independently 0 to 3; and from 0 to 90% by weight based on the total weight of surfactant of ether carboxylate.

2. A solution according to claim 1 wherein the glyphosate is present as its ammonium, C$_2$ to $_3$ amine, alkanolanine or methosulphate salt.

3. A solution according to claim 1 which additionally comprises an amphoteric surfactant.

4. A solution according to claim 1 comprising up to 15 % by weight of a wetting agent.

5. A solution according to claim 1 comprising up to 5 % by weight of a chelant.

6. A solution according to claim 5 wherein the chelant is an amino phosphonate.

7. A solution according to claim 1 having a pH between 4.5 and 5.5.

8. A composition according to any foregoing claim containing at least 10% of an ether carboxylate which is a compound of the formula RO[CH$_2$CH$_2$O]$_m$CH$_2$CO$_2$M where R is an alkyl, alkenyl or alkylphenol group having from 6 to 20 aliphatic carbon atoms m is 1 to 30 and M is potassium, ammonium or an amine.

9. A process for preparing a glyphosate solution concentrate comprising mixing water, a water-soluble glyphosate salt, an alkyl ether carboxylate, and an amido alkyl amine oxide.

10. A process according to claim 9 in which said glyphosate solution concentrate comprises, by weight of the blend, 10 to 70% ether carboxylate, 20 to 80% amidoalkylamine oxide and further comprising 5 to 40% of a material selected from the group consisting of: water miscible mono- di- or polyhydroxy alcohol and alcohol ether.

11. A herbicidal spray prepared by diluting a solution concentrate according to claim 1 with water.

12. A solution according to claim 2 further comprising an amphoteric surfactant.

13. A solution according to claim 2 further comprising up to 15% by weight of a wetting agent.

14. A solution according to claim 3 further comprising up to 15% by weight of a wetting agent.

15. A solution according to claim 2 further comprising up to 5% by weight of a chelant.

16. A solution according to claim 3 further comprising up to 5% by weight of a chelant.

17. A solution according to claim 4 further comprising up to 5% by weight of a chelant.

18. A solution according to claim 2 having a pH between 4.5 and 5.5.

19. A solution according to claim 3 having a pH between 4.5 and 5.5.

20. A solution according to claim 5 having a pH between 4.5 and 5.5.

* * * * *